United States Patent [19]

Garosi

[11] Patent Number: 5,704,940
[45] Date of Patent: Jan. 6, 1998

[54] INSTRUMENT SET FOR PREPARATION OF THE SEAT FOR THE FEMORAL COMPONENT OF A NON-CEMENTED HIP PROSTHESIS

[76] Inventor: Piero Garosi, Via Medaglie d'oro, 13 - 50057 Ponte a Elsa - Firenze, Italy

[21] Appl. No.: 723,153

[22] Filed: Sep. 30, 1996

[30] Foreign Application Priority Data

Oct. 3, 1995 [IT] Italy ................................. FI95A0204

[51] Int. Cl.⁶ ............................................. A61B 17/56
[52] U.S. Cl. ............................................. 606/85; 606/80
[58] Field of Search .................... 606/79, 80, 85, 606/99

[56] References Cited

U.S. PATENT DOCUMENTS 5,089,004  2/1992  Averill et al. ........................ 606/85
5,607,431  3/1997  Dudasik et al. ...................... 606/80

*Primary Examiner*—Michael Buiz
*Assistant Examiner*—David O. Reip
*Attorney, Agent, or Firm*—McGlew and Tuttle

[57] ABSTRACT

The rasps of a first set of metaphyseal rasps are capable of working, in a first stage, the femoral canal in the zone of the metaphysis until the bony part K1, K2 is reached and cut into to form the metaphyseal seat for a femoral component of a hip prosthesis, the rasps having guide stems which act in the zone of the diaphysis. The rasps of a second series of sub-metaphyseal and diaphyseal rasps are capable of working, in a second stage, the femoral canal in the sub-metaphyseal zone and the adjacent zone of the diaphysis, until the bony part K3 is reached and cut into to complete the seat for the femoral component.

3 Claims, 2 Drawing Sheets

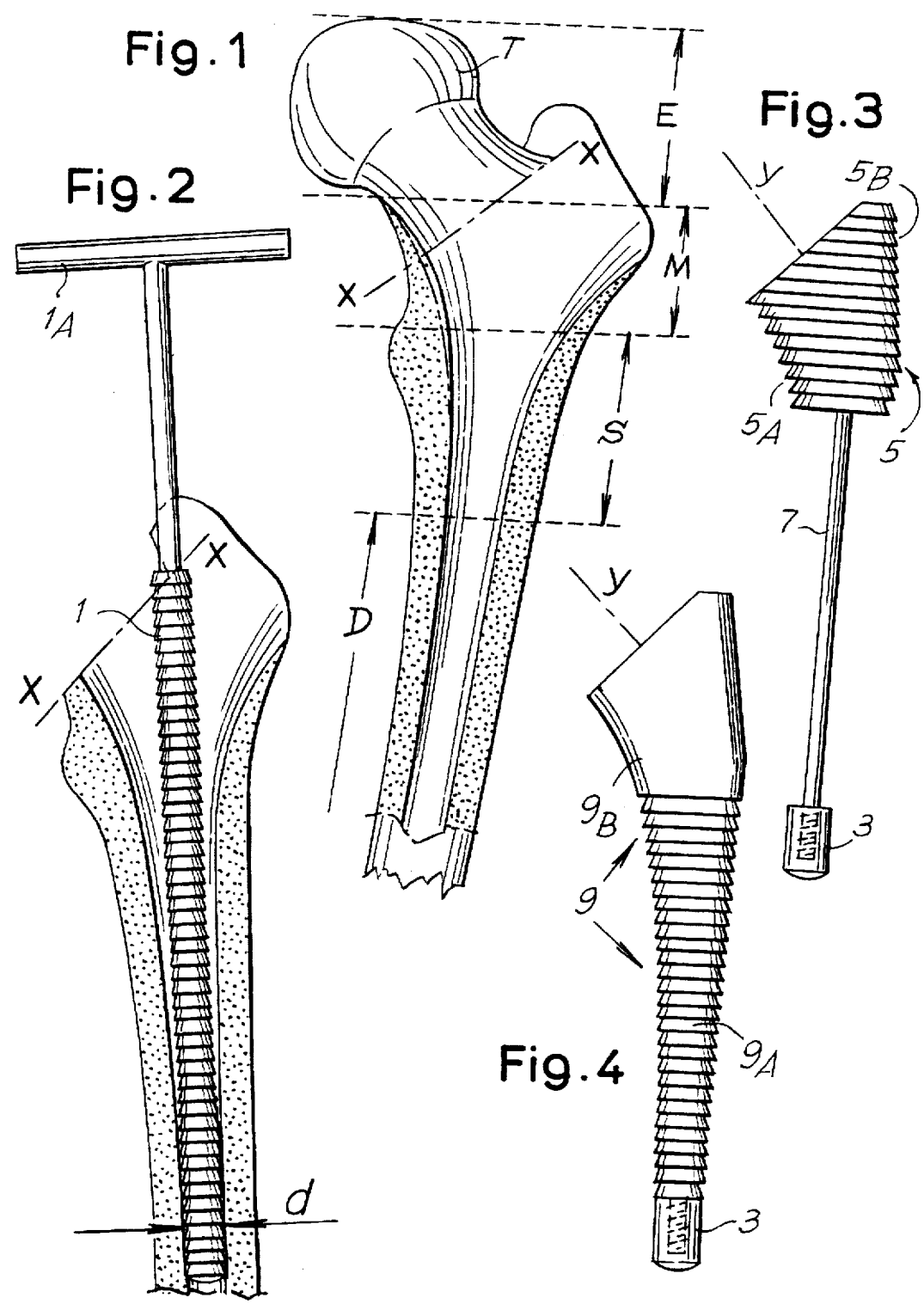

INSTRUMENT SET FOR PREPARATION OF THE SEAT FOR THE FEMORAL COMPONENT OF A NON-CEMENTED HIP PROSTHESIS

DESCRIPTION

The correct installation of the femoral component of a non-cemented hip prosthesis presupposes a stability afforded by the prosthesis/bone contact (fit) and a maximum filling of the bone cavity (fill), on which the fit depends, in the femoral metaphysial zone.

The possibility of obtaining optimum conditions in the metaphysial zone with current femoral rasps is small in terms of percentage because of the morphology of the femur itself. Although this is possible in a "cylindrical" femur, it is unrealizable in a "flute"-shaped femur and even more so in a "trumpet"-shaped femur; this is because, as the femoral metaphysis is very large, a prosthetic stem of great size would be required to fill it, but this becomes impossible because the sub-metaphysial zone of the prosthesis will be too large in relation to the sub-metaphysial zone of the femur; for this reason, when using femoral rasps which increase in size in the preparation of the prosthetic housing, it is necessary to stop at measurements which are less than ideal, because there will be a sub-metaphysial and not metaphysial fit and thus an underdimensioned metaphysial fill.

With the installation technique and the instrument set according to the invention, it has been possible to overcome these problems, thus obtaining a virtually total filling of the metaphysial and sub-metaphysial zone of the femur, a fundamental precondition for an optimum metaphysial fit which allows correct transmission of the loads from the prosthetic stem to the bone.

Research into achieving these conditions had led—in the past—to so-called custom-made prostheses being devised, which achieved the appointed purpose because they were designed by computer, individually, starting with a C.A.T. of the hip carried out beforehand. Although this type of prosthesis can be justified in the treatment of tumoral forms, because of the loss of substance involved, it cannot in the treatment of arthrotic pathology of the coxofemoral joint, because of both the high cost and the quality control, and also because of the complexity of organization and planning, as a result of which this solution would be truly unmanageable, given the high number of prosthetic installations which are carried out around the world every year.

Until today, the custom-made concept has been interpreted and effected by morphological and dimensional adaptation of the prosthesis to the bone. According to the invention, however, the custom-made concept is effected by adaptation of the femur to the prostheses at surgical level, thus avoiding all the problems explained above.

The subject of the invention is therefore an instrument set for preparation of the seat of the femoral component of a non-cemented hip prosthesis, which instrument set comprises: a first series of metaphysial rasps, each capable of working, in a first stage, the zone of the metaphysis until the bony part is reached and if necessary cut into to form the metaphysial seat, with guide means acting in the zone of the diaphysis; and a second series of sub-metaphysial rasps with a diaphysial guide, capable of working, in a second stage, the sub-metaphysial zone and the adjacent zone of the diaphysis, until the bony part is reached and cut into to complete the seat for said femoral component. The femoral component of the prosthesis corresponds to the shape of the seat obtained with the two series of abovementioned instruments.

Each rasp of the first series has a stem-type appendage which extends along the diaphysis and has a terminal or distal end calibrated to the internal dimension of the cavity of the femur in this zone; guidance of said first rasp is thus ensured.

At the end of the rasps of the second series, means are provided for engaging a similar calibrated terminal or distal end.

The instrument set in question advantageously also comprises an auxiliary instrument capable of acting inside the zone of the diaphysis, for the preparation of the seat for said terminal or distal end.

The invention will be better understood by following the description and the attached drawing which shows a practical non-limiting embodiment of the invention itself, and in which FIG. 1 shows in brief the upper part of a femur;

FIG. 2 shows a preliminary operation for preparation of the diaphysis;

FIGS. 3 and 4 show separately the active parts of two rasp-type instruments for preparation of the metaphysial zone and of the sub-metaphysial zone and of an adjacent portion of the diaphysis;

Figure 5:
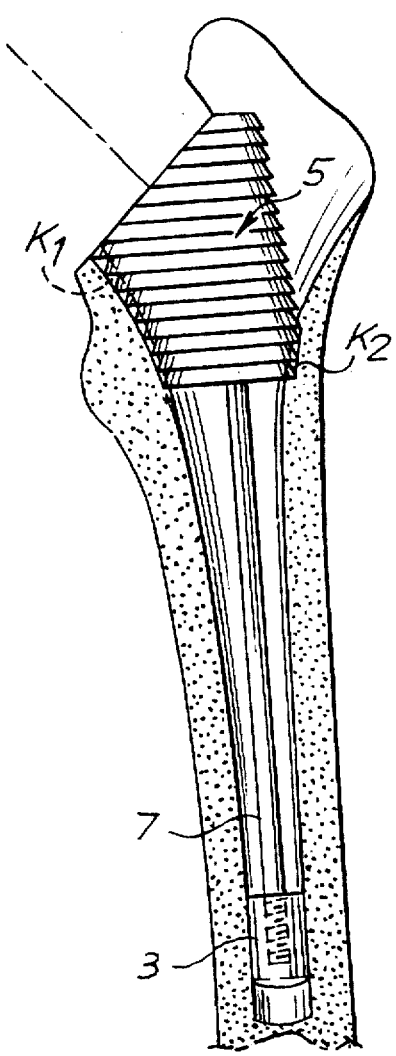
FIGS. 5 and 6 show how the two rasp-type instruments are used.

In the drawings, the femur is illustrated with the cortical part hatched.

In FIG. 1, the illustrated part of the femur is still complete with the head T which is sectioned on the plane X—X; of the illustrated part of the femur, the zone of the epiphysis is indicated by E, the zone of the metaphysis by M, the sub-metaphysial zone by S and the part of the diaphysis, which is illustrated in part, by D.

As can be seen from FIG. 2, after cutting along the plane X—X as mentioned above, use is made of an auxiliary instrument 1 which can be maneuvered by means of a conventional handle 1A and which is made to penetrate the zone of the diaphysis to detect the size of the zone of the diaphysis which corresponds to the lower end of the femoral component, the seat of which can be prepared with the instrument set in question. The auxiliary instrument 1 prepares the zone of the diaphysis for the definition of the dimension, indicated by d, of the femoral canal at that point, for the distal end of the prosthesis and for those of the instrument set for preparation of the seat. The subsequent preparation of the seat with the two rasps will be carried out with a corresponding distal end 3 which allows centering of the rasps themselves. The instrument 1 can be used to reach the rigid tubular bony zone of the femur in the zone of said distal end, for said purpose of guidance.

5 (see FIG. 3) indicates a first rasp-type instrument of a series of instruments 3 of increasing sizes intended for the preparation of the zone of the metaphysis; use will be made of the successive instruments of the series which gradually increase in size until fill and fit are achieved in the metaphysis; each rasp-type instrument 5 will be equipped with a handle to be applied along the y axis which is inclined in a corresponding manner to the orientation of the head T of the femur, and also equipped with a stem 7 to which can be fitted a distal end 3 corresponding to the seat prepared for the distal end of the femoral component of the hip prosthesis to be used. The rasp-type instrument 5 has its active zone shaped as shown in the drawing and in particular with two profiles 5A and 5B which are then suitably interconnected in the zones which correspond to the view in FIG. 3.

9 (see in particular FIG. 4) indicates a second rasp-type instrument of a series of gradually increasing sizes to be used for the preparation of the sub-metaphysial zone and of the adjacent zone of the diaphysis until use is made of the rasp 9 corresponding to the last rasp 5 used. Preparation is thus effected for the application of the non-cemented femoral component. The active zone of these rasp-type instruments 9 is indicated by 9A while the part 9B above corresponds to the shape of the seat which is obtained with the last of the first rasp-type instruments 5 (see FIG. 3) used in the first stage. Each of said second rasp-type instruments 9 will always be maneuvered by a handle applied along the y axis and will be equipped with a distal end 3 corresponding to the dimensions indicated by the instrument 1.

In a first stage of the preparation of the seat, with the aid of the rasps 5 (see FIG. 5) and with the distal end 3 applied to the stem 7 of these, excavation of the spongy part of the metaphysial zone of the femur is achieved, with partial removal of the hard part in the zone indicated by K1 and also in part in the zone indicated by K2; the zone K1 is also shown by a broken line in FIG. 1. The portion K1 and if appropriate the portion K2 of the bony part which is removed with the first rasp-type instruments 5 will depend on the specific morphology of the femur in which the seat for the femoral component of the prosthesis is being excavated. The result of this is that a very accurate seat is formed which corresponds to the shape in the metaphysial zone of the femoral component of the prosthesis to be adopted, thus succeeding in ensuring complete support for the non-cemented prosthesis in the zone of the metaphysis, and over an area which is certainly very strong because it ensures there is no residue of spongy zone inside the bone.

Figure 6:
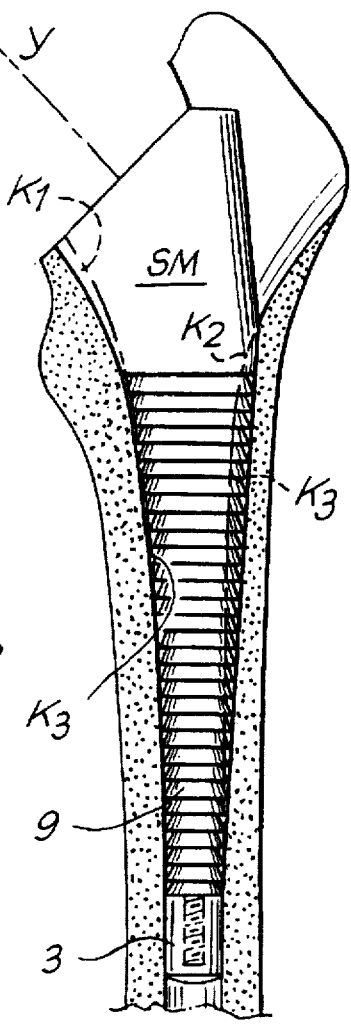

After the first stage of working has been carried out, use is made of the rasp-type instruments 9 (FIG. 4) of the second series, to carry out the second stage of the operation which is shown in FIG. 6. The rasp-type instruments 9 are inserted into the seat already established by working by means of the first rasp-type instruments 5; the rasps 9 are also guided by a distal end 3. There is thus formed—with the second stage of the preparation operation—a seat which corresponds exactly to the shape of the last of the rasp-type instruments 9 used, which also acts on the hard strong part of the bone, bringing about a removal of the portions K3 and if appropriate of other internal surface portions of the hard part of the bone, making sure that there is no residual spongy part.

Figure 7:
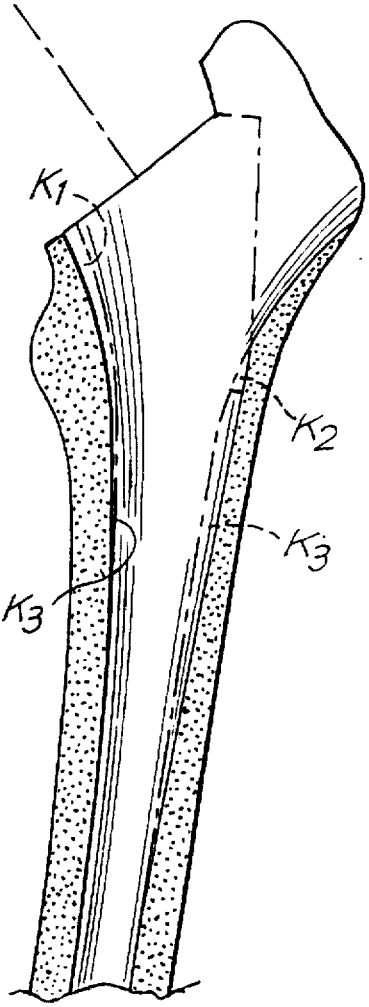
FIG. 7 shows the result of the preparation.

In the two operational stages for preparation of the seat, which in the end is as shown in FIG. 7, the operations are facilitated by the presence of the guide which is created by the distal ends 3 which are present on the rasp-type instruments 5 and 9 and act in the zone of the diaphysis previously prepared to receive and guide the distal ends 3 during the operations for preparation of the seat with the rasp-type instruments 5 and 9. If the distal end of the prosthesis established by the last of the rasps 5 used is larger than the dimension d (FIG. 2), action is taken with instruments 1 to enlarge the femoral canal to the dimension of the prosthesis defined above. The seat thus prepared therefore corresponds completely to a prefabricated prosthesis.

The femoral component of the non-cemented hip prosthesis will have exactly the shape corresponding to that of the seat which is excavated using the instruments 5 and 9 themselves; the operating technique according to the invention is therefore to create the seat corresponding to the prosthesis rather than to adapt the prosthesis to a seat made according to only the natural morphological characteristics of the femur which is to be equipped with the hip prosthesis.

It is intended that the drawing shows only an exemplary embodiment given only as a practical demonstration of the invention, it being possible for this invention to vary in form and arrangement without however leaving the scope of the concept which informs the invention. The presence of any reference numbers in the attached claims has the aim of facilitating reading of the claims with reference to the description and the drawing, and does not limit the scope of protection represented by the claims.

I claim:

1. A set of instruments for preparing the femur canal of a femur for receiving a non-cemented hip prosthesis, comprising:

an elongated reamer tool having a uniform diameter, said reamer tool being configured for reaming the diaphyseal zone of the femoral canal for preparing the diaphysis to receive a distal portion of said hip prosthesis;

a series of metaphyseal rasps, each of said metaphyseal rasps being a different size and comprising a proximal cutting portion and a distal guiding means, said proximal cutting portion having bone cutting teeth for cutting only the metaphyseal zone of the femoral canal for preparing the metaphysis to receive a proximal portion of said hip prosthesis, and said distal guiding means having a smooth, non-cutting portion for guiding said metaphyseal rasp in said femoral canal; and a series of sub-metaphyseal rasps, each of said sub-metaphyseal rasps being a different size and comprising a proximal portion, a medial cutting potion, and a distal guiding means, said proximal portion having a smooth, non-cutting surface, said medial cutting portion having bone cutting teeth for cutting only the sub-metaphyseal zone of the femoral canal for preparing the sub-metaphysis to receive a medial portion of a hip prosthesis, and said distal guiding means having a smooth, non-cutting portion for guiding said sub-metaphyseal rasp in said femoral canal.

2. The set of instruments as set forth in claim 1, wherein the distal guiding means of the series of metaphyseal rasps comprises a stem-shaped elongated portion for extension along the diaphysis, and further comprises an interchangable tip portion having a diameter sized to correspond to the diameter of the reamer tool, whereby the tip portion closely fits a reamed femoral canal and serves to guide the metaphyseal rasps during a rasping procedure.

3. The set of instruments as set forth in claim 1, wherein the distal guiding means of the series of sub-metaphyseal rasps comprises an interchangable tip portion having a diameter sized to correspond to the diameter of the reamer tool, whereby the tip portion closely fits a reamed femoral canal and serves to guide the sub-metaphyseal rasps during a rasping procedure.

* * * * *